(12) United States Patent
Wolleb et al.

(10) Patent No.: US 6,743,926 B2
(45) Date of Patent: Jun. 1, 2004

(54) PROCESS FOR THE PREPARATION OF INDOLE DERIVATIVES AND INTERMEDIATES OF THE PROCESS

(75) Inventors: Annemarie Wolleb, Fehren (CH); Heinz Wolleb, Fehren (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/296,106

(22) PCT Filed: May 17, 2001

(86) PCT No.: PCT/EP01/05667

§ 371 (c)(1), (2), (4) Date: Nov. 22, 2002

(87) PCT Pub. No.: WO01/92223

PCT Pub. Date: Dec. 6, 2001

(65) Prior Publication Data

US 2003/0166946 A1 Sep. 4, 2003

(51) Int. Cl.$^7$ .............................................. C07D 209/18

(52) U.S. Cl. ..................................................... 548/494

(58) Field of Search .......................................... 548/494

(56) References Cited

U.S. PATENT DOCUMENTS

| | | | |
|---|---|---|---|
| 4,571,428 A | 2/1986 | Kapa | 556/437 |
| 4,650,890 A | 3/1987 | Jewell, Jr. et al. | 556/446 |
| 4,677,211 A | 6/1987 | Jewell, Jr. et al. | 548/491 |
| 4,739,073 A | 4/1988 | Kathawala | 548/406 |
| 4,870,199 A | 9/1989 | Chen et al. | 556/437 |
| 5,356,896 A | 10/1994 | Kabadi et al. | 514/256 |

FOREIGN PATENT DOCUMENTS

| | | |
|---|---|---|
| EP | 0114027 | 7/1984 |
| EP | 0244364 | 11/1987 |
| EP | 0363934 | 4/1990 |
| EP | 0470039 | 2/1992 |
| WO | 99/47474 | 9/1999 |

OTHER PUBLICATIONS

O. Tempkin et al., Tetrahedron, vol. 53, No. 31, pp. 10659–10670, (1997).

(List continued on next page.)

*Primary Examiner*—Joseph K. McKane
*Assistant Examiner*—Sonya Wright
(74) *Attorney, Agent, or Firm*—Kevin T. Mansfield

(57) ABSTRACT

A process for the preparation of compounds of formula (1), wherein $R_1$ is $C_1-C_6$alkyl and X is hydrogen, a hydrocarbon radical or a cation, wherein a compound of formula (2), wherein $R_1$ is as defined above and $R_2$ is hydrogen or a hydrocarbon radical, is reduced, the resulting compound of formula (3) is reacted with a compound that introduces the radical of formula $-CH_2-COOR_3$, wherein $R_3$ has the meanings given above for $R_2$, and the resulting compound of formula (4) is reduced and optionally hydrolysed.

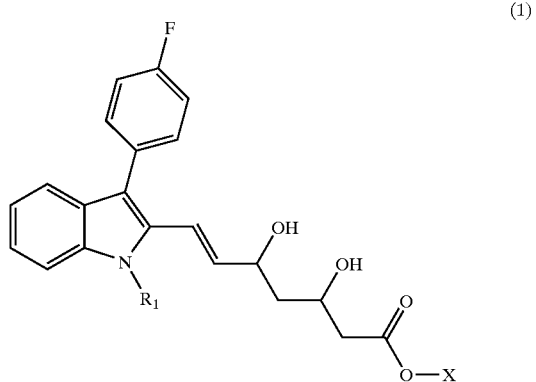

(1)

(2)

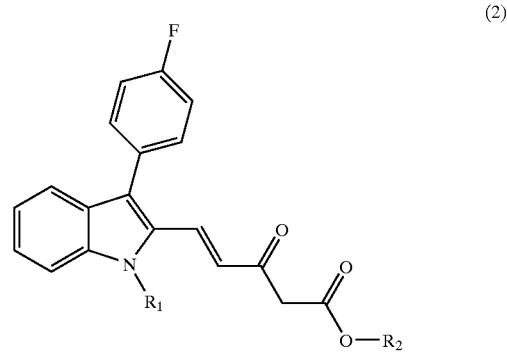

(3)

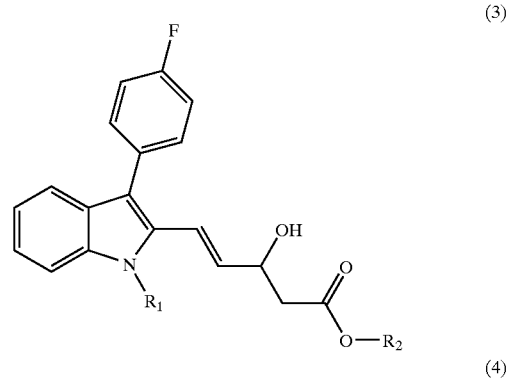

(4)

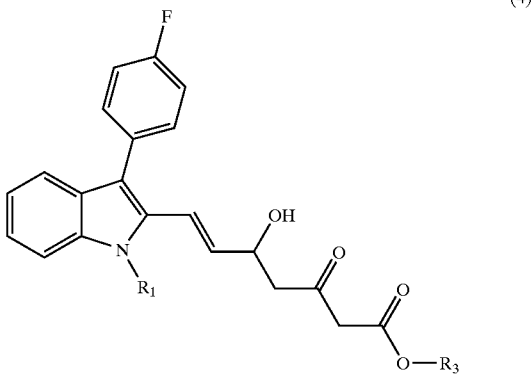

12 Claims, No Drawings

OTHER PUBLICATIONS

F. Kathawala et al., Helvetica Chimica Acta, vol. 69 (1986) pp. 803–805.

J. E. Lynch et al., Tetrahedron Letters, vol. 28, No. 13, pp. 1385–1388, (1987).

A. Katritzky et al., J. Org. Chem., vol. 60, pp. 3707–3710, (1995).

M. Brennan et al., Heterocycles, vol. 24, No. 10, pp. 2879–2885, (1986).

R. Liu et al., J. Org. Chem., vol. 62, pp. 7447–7456, (1997).

P. Zhang et al., Tetrahedron Letters, vol. 36, No. 18, pp. 3103–3106, (1995).

J. Bergman et al., J. Org. Chem., vol. 57, pp. 2495–2497, (1992).

L. Chu et al., Tetrahedron Letters, vol. 38, No. 22, pp. 3871–3874, (1997).

P. Grieco et al., J. Am. Chem. Soc., vol. 110, pp. 1630–1631, (1988).

T. Gilchrist et al., Tetrahedron, vol. 53, No. 12, pp. 4447–4456, (1997).

A. Cotterill et al., Tetrahedron, vol. 51, No. 26, pp. 7223–7230, (1995).

M. Rathke et al., J. Org. Chem., vol. 50, pp. 2624–2626, (1985).

L. Ouellet et al., Synlett, Jun. 1997, pp. 689–690.

Kiyooka et al., Tetrahedron Letters, vol. 27, No. 26, pp. 3009–3012, (1986).

W. Wierenga et al., J. Org. Chem., vol. 44, No. 2, (1979), pp. 310–311.

J. Turner et al., J. Org. Chem., vol. 54, pp. 4229–4231, (1989).

J. Boutagy et al., Chemical Reviews, vol. 74, No. 1, pp. 87–99, (1974).

D. Netz et al., Tetrahedron Letters, vol. 33, No. 15, pp. 1957–1958, (1992).

E. Baader et al., Tetrahedron Letters, vol. 30, No. 38, pp. 5115–5118, (1989).

S. Ohta et al., Communications, Jan. 1985, pp. 45–48.

J. March, Advanced Organic Chemistry, Reactions, Mechanisms, and Structure, $4^{th}$ Ed., pp. 542–543 (1992).

M. Kinugawa et al., J. Chem. Soc. Perkin Trans. 1, (1995), pp. 2677–2678.

A. Nudelman et al., Synthesis, No. 4, (1999), pp. 568–570.

R. Phillips et al., J. Am. Chem. Soc., (1986), vol. 108, pp. 2023–2030.

PROCESS FOR THE PREPARATION OF INDOLE DERIVATIVES AND INTERMEDIATES OF THE PROCESS

This application is a 371 of PCT/EP01/015667 filed May 17, 2001.

The present invention relates to a process for the preparation of indole derivatives and to novel intermediates.

Indole derivatives of the formula (1) hereinbelow are known as pharmaceutical active ingredients (e.g. from U.S. Pat. No. 4,739,073). Fluvastatin, an HMG-CoA reductase inhibitor, that is, a cholesterol-biosynthesis inhibitor, is an important indole derivative that is used in the treatment of hyperlipoproteinaemia and arteriosclerosis.

Known processes for the preparation of the indole compounds of formula (1) do not in all cases meet the demands made in terms of yield and economy of the process.

It is accordingly the aim of the present Application to make available a novel process for the preparation of indole compounds of formula (1) by means of which such compounds can be obtained in as high a yield as possible.

The present invention thus relates to a process for the preparation of compounds of formula

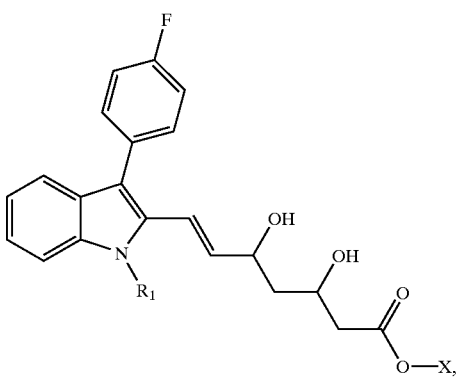

(1)

wherein $R_1$ is $C_1$–$C_6$alkyl and
X is hydrogen, a hydrocarbon radical or a cation,
in which process a compound of formula

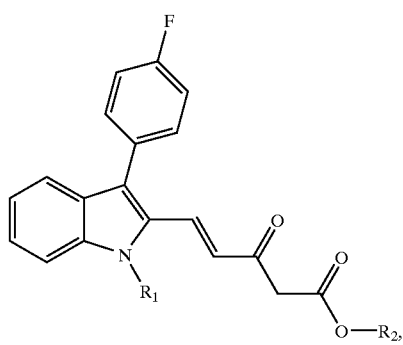

(2)

wherein $R_1$ is as defined above and $R_2$ is hydrogen or a hydrocarbon radical, is reduced, the resulting compound of formula

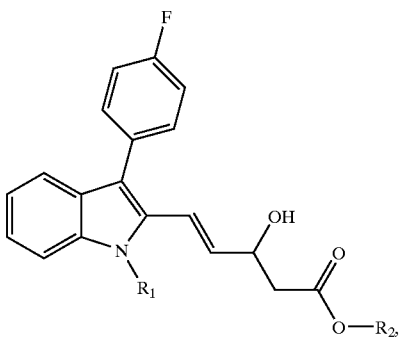

(3)

wherein $R_1$ and $R_2$ are as defined above, is reacted with a compound that introduces the radical of formula —$CH_2$—$COOR_3$ wherein $R_3$ has the meanings given above for $R_2$, and the resulting compound of formula

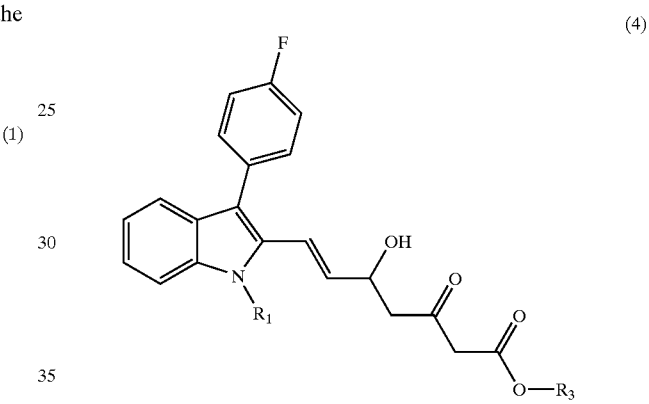

(4)

is reduced and optionally hydrolysed.

There come into consideration as $C_1$–$C_6$alkyl radicals for $R_1$, for example, methyl, ethyl, n- or iso-propyl, n-, iso-, sec- or tert-butyl, and straight-chain or branched pentyl or hexyl. $C_1$–$C_4$Alkyl radicals are preferred. $R_1$ is preferably propyl, especially isopropyl.

There come into consideration as hydrocarbon radicals for $R_2$, $R_3$ and X, each independently of the others, for example unsubstituted or substituted alkyl, alkenyl, alkynyl and phenyl radicals. Special mention may be made of unsubstituted or substituted $C_1$–$C_{12}$alkyl, $C_3$–$C_{12}$-alkenyl, $C_3$–$C_{12}$alkynyl and phenyl radicals. Preferably, $R_2$, $R_3$ and X are each independently of the others unsubstituted or substituted alkyl radicals, especially $C_1$–$C_{12}$alkyl radicals and preferably $C_1$–$C_6$alkyl radicals. There may be mentioned as an example of substituents of the alkyl radicals, for example, phenyl that is unsubstituted or further substituted on the phenyl ring by nitro or by hydroxy. There may be mentioned as examples of $R_2$, $R_3$ and X methyl, ethyl, n- or iso-propyl, n-, iso-, sec- or tert-butyl, allyl, benzyl, nitrobenzyl and also hydroxybenzyl. $R_2$, $R_3$ and X are especially preferably $C_1$–$C_4$alkyl. $R_2$ is more especially preferably methyl or ethyl, especially methyl. $R_3$ and X are more especially preferably butyl, especially tert-butyl.

When the radical X is a cation, it may be, for example, sodium or potassium, especially sodium.

The reduction of the compound of formula (2) to the compound of formula (3) can be carried out according to commonly used methods, such as are described, for example, in Houben-Weyl, Methoden der organischen Chemie, Volume 7/2b, pages 1991 ff, Georg Thieme Verlag, Stuttgart, 1976. The reduction can be effected, for example, with a metal hydride, such as lithium aluminium hydride, diisobutylaluminium hydride or, especially, sodium borohydride, in an anhydrous, inert organic solvent, for example an ether, such as tetrahydrofuran, diethyl ether, 1,2-dimethoxyethane or 1,2-diethoxyethane. When sodium borohydride is used, it is preferable to use as solvent a mixture of such ethers with a lower alcohol, especially methanol. There comes into consideration as the temperature for the reaction, for example, a range of from −80 to 25° C. Preferably, the reaction is carried out in an inert gas atmosphere.

The reaction of the compound of formula (3) to form the compound of formula (4) can be carried out, for example, according to the procedure described in U.S. Pat. No. 4,870,199. For example a compound of formula $CH_3—COOR_3$, such as tert-butyl acetate, may be used as the compound that introduces the radical of formula $—CH_2—COOR_3$, $R_3$ having the meanings and preferred meanings mentioned above. The reaction is generally so carried out that, in the presence of a strong base, such as lithium diisopropylamide, a monoanion of the compound of formula $CH_3—COOR_3$ is formed. The reaction is usually performed in an anhydrous, inert organic solvent, for example an ether, such as diethyl ether, 1,2-dimethoxyethane, 1,2-diethoxyethane or, especially, tetrahydrofuran, the reaction generally being carried out in an inert gas atmosphere, at a temperature of from −80 to 25° C. In a next step, the monoanion formed is reacted with the compound of formula (3), that reaction usually being performed in the same solvent and in an inert gas atmosphere, at a temperature of, for example, from −80 to 25° C.

The reduction of the compound of formula (4) can be carried out, for example, by way of a cyclic boronate using sodium borohydride, as in O. Tempkin, Tetrahedron, Vol. 53, No. 31, 10659–10670 (1997). The reduction is effected, for example, in an ether and/or lower alcohol, such as tetrahydrofuran or methanol, at a temperature of, for example, from −50 to −80° C. As borane there comes into consideration, for example, diethyl methoxyborane. The reduction can alternatively be carried out with diisobutylaluminium hydride or tributyltin hydride, as described in S. Kiyooka, Tetrahedron Letters, Vol. 27, No. 26, 3009–3012 (1986), or with zinc borohydride, as described in F. Kathawala, Helv. Chim. Acta, Vol. 69, 803–805 (1986). The reduction can also be carried out with $NaBH_4$ in the presence of triethylboranes as complexing agents, as described in U.S. Pat. No. 4,739,073.

The hydrolysis of the compound obtained after reduction of the compound of formula (4) can be carried out, for example, by conventional basic hydrolysis of the ester. For that purpose, the compound obtained after reduction of the compound of formula (4) is treated with approximately one mole of an inorganic base, such as an alkali metal hydroxide, for example potassium hydroxide or, especially, sodium hydroxide, in a mixture of water and a water-miscible organic solvent, for example a lower alcohol or an ether, such as methanol, ethanol or tetrahydrofuran, at a temperature of, for example, from 0 to 80° C. It is also possible to proceed with slightly less than the stoichiometric amount of base and then remove excess ester by means of extraction with a water-immiscible organic solvent, for example tert-butyl methyl ether; freeze-drying can then be carried out. In order to form the free acid, the ester can also be hydrolysed in an acidic medium, it being possible for such a hydrolysis to be carried out according to procedures known per se. It is preferable, following the reduction of the compound of formula (4), for hydrolysis, preferably with sodium hydroxide, to be carried out.

The compounds of formula (2) are novel and can be obtained, for example, according to the following processes:

According to a process variant a) for the preparation of compounds of formula (2), a compound of formula

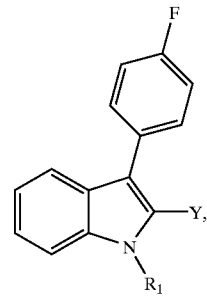

(5)

wherein $R_1$ has the meanings and preferred meanings given hereinbefore and Y is bromine, chlorine, iodine, $—OSO_2CF_3$ or $—COCl$, especially bromine, is reacted with a compound that introduces the radical of formula $—CH=CH—Z$, wherein Z is the radical $—COOR_4$, $—COR_5$ or $—CN$, $R_4$ is hydrogen or a hydrocarbon radical and $R_5$ is a hydrocarbon radical or unsubstituted or substituted amino, and the resulting compound of formula

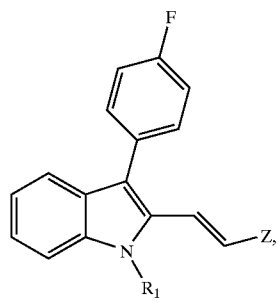

(6)

optionally after conversion of the compound of formula (6) wherein Z is the radical $—COOR_4$ into the corresponding acid chloride or into the free acid, is reacted with a compound that introduces the radical of formula $—CH_2—COOR_2$.

When $R_4$ and $R_5$ are hydrocarbon radicals, the meanings and preferred meanings for hydrocarbon radicals given hereinbefore for $R_2$ apply. For $R_5$ as unsubstituted or substituted amino there comes into consideration, for example, amino substituted by $C_1$–$C_{12}$alkyl and/or by $C_1$–$C_{12}$alkoxy. In that case there preferably comes into consideration a radical of formula $—N(OR_6)R_7$ wherein $R_6$ and $R_7$ are hydrogen or hydrocarbon radicals, especially $C_1$–$C_6$alkyl and preferably methyl.

When $R_6$ and $R_7$ are hydrocarbon radicals, the meanings and preferred meanings for hydrocarbon radicals given hereinbefore for $R_2$ apply.

Preferred as radicals Z are the radicals of formula $—COOR_4$ or $—CO—N(OR_6)R_7$ wherein $R_4$, $R_6$ and $R_7$ have the meanings and preferred meanings given hereinbefore.

The compounds of formulae

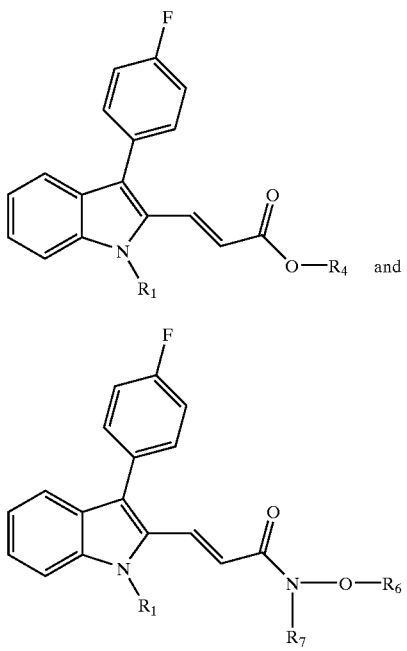

are therefore of particular importance as compounds of formula (6).

The reaction of the compound of formula (5) to form the compound of formula (6) can be carried out according to methods known per se. The process can be carried out, for example, by the so-called Heck reaction, in which especially aromatic iodine or bromine compounds are reacted with olefins in the presence of palladium catalysts. The methodology is described, for example, in R. F. Heck, Acc. Chem. Res. 1979, 12,146; R. F. Heck, Org. React. 1982, 27, 345; and in R. F. Heck, Palladium Reactions in Synthesis, Academic Press, London 1985, S. Bräse and A. De Meijere in Metal-catalyzed Cross-coupling Reactions, Chapter 3, Wiley-VCH, DE-Weinheim 1998 and in WO-A-99/47474.

There come into consideration as palladium catalysts especially those described under the general formula (Vlla) in WO-A-99/47474, preferably the catalysts denoted K1 to K11 in the examples documented in that specification, it being possible for the catalysts to be used especially in the amounts indicated therein.

As compounds that introduce the radical of formula —CH=CH—Z wherein Z is —COOR$_4$ there come into consideration, for example, those of formula CH$_2$=CH—COOR$_4$, for example acrylic acid. As compounds that introduce the radical of formula —CH=CH—Z wherein Z is —CO—N(OR$_6$)R$_7$ there come into consideration, for example, those of formula CH$_2$=CH—CO—N(OR$_6$)R$_7$, for example N-methoxy-N-methylacrylamide. Mention may also be made of the compound of formula CH$_2$=CH—CN as compound that introduces the radical of formula —CH=CH—Z.

The molar ratio of the reaction partners (compound of formula (5)/compound introducing the radical of formula —CH=CH—Z) of such coupling reactions is generally in the range from 1:1 to 1:10, with preference being given to a ratio in the range from 1:1 to 1:2. The reaction is carried out with cooling up to the boiling temperature of the solvent, especially at from room temperature up to the boiling temperature of the solvent (reflux conditions). Suitable solvents are customary, especially higher-boiling, solvents, for example non-polar aprotic solvents, e.g. xylene or toluene, or polar aprotic solvents, e.g. dimethylformamide, dimethoxyethane or dimethylacetamide. The reaction product (6) obtainable can be worked up and isolated in a manner known per se by means of customary purification methods, for example by removal of the solvent and subsequent separation procedures, for example fine distillation, recrystallisation, preparative thin-layer chromatography, column chromatography or preparative gas chromatography.

When, in the resulting compound of formula (6), Z is the radical —COOR$_4$ and R$_4$ is a hydrocarbon radical, that compound can subsequently be converted into the free acid by acid hydrolysis of the ester. If desired, that compound can be converted into the acid chloride before being further reacted. Both the acid hydrolysis and the conversion into the acid chloride can be effected in conventional manner according to known procedures.

The reaction of the compound of formula (6), especially the compound of formula (7), with a compound that introduces the radical of formula —CH$_2$—COOR$_2$ can be carried out, for example, as described in A. Nudelman, Synthesis, No. 4, 568–570 (1999). The conversion of the compound of formula (6) into the acid chloride and the reaction with a compound that introduces the radical of formula —CH$_2$—COOR$_2$ can be carried out, for example, as in W. Wierenga, J. Org. Chem., Vol. 44, No. 2, 310–311 (1979). As compounds that introduce the radical of formula —CH$_2$—COOR$_2$ there may be mentioned, for example, compounds of the formula HOOC—CH$_2$—COOR$_2$, such as monomethyl malonate or monoethyl malonate, such compounds being understood as including also salts thereof, for example the potassium salt.

The reaction of the compound of formula (6), especially of the compound of formula (8), with a compound that introduces the radical of formula —CH$_2$—COOR$_2$ can be carried out, for example, analogously to the process described above for the reaction of the compound of formula (3) to form the compound of formula (4). As compounds that introduce the radical of formula —CH$_2$—COOR$_2$ there may be mentioned in that connection, for example, compounds of the formula CH$_3$—COOR$_2$, such as ethyl acetate. A typical reaction by means of a Claisen reaction is described in J. A. Turner, J. Org. Chem., Vol. 54, 4229–4231 (1989).

The compound of formula (5) can be obtained, for example, by halogenating a corresponding compound in which Y is hydrogen. The halogenation can be carried out according to generally known methods. For the bromination, reference is made, for example, to Houben-Weyl, Methoden der organischen Chemie, Volume 5/4, pages 233 if, Georg Thieme Verlag, Stuttgart, 1960. There come into consideration for the bromination, for example, elemental bromine, N-bromosuccinimide, pyridinium bromide perbromide or triphenylphosphine dibromide, in an inert, preferably halogenated solvent, such as carbon tetrachloride, chloroform, chlorobenzene or dichlorobenzene. The bromination is generally carried out at a temperature of from −5 to 25° C., and in the case of N-bromosuccinimide at approximately from 40 to 85° C.

The starting compounds wherein Y is hydrogen are known or can be obtained analogously to known procedures, for example the procedures indicated in U.S. Pat. No. 4,739,073.

According to a further process variant b) for the preparation of compounds of formula (2), a compound of formula

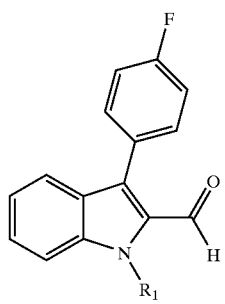

(9)

is reacted with a compound of formula CH$_3$—CO—CH$_2$—COOR$_2$ and, optionally, then with a compound that introduces a protecting group, to form a compound of formula

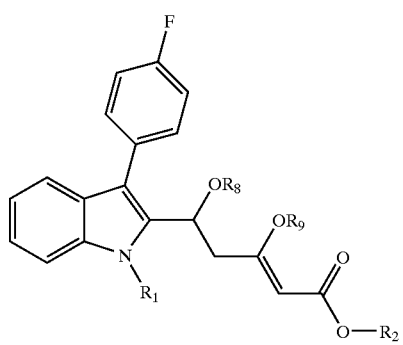

(10)

wherein R$_1$ and R$_2$ have the meanings and preferred meanings indicated hereinbefore and R$_8$ $_{and\ R9}$ are hydrogen or a protecting group,
a double bond is introduced under acidic or basic conditions, and any protecting group that may be present is removed.

As compounds that introduce a protecting group it is possible to use the compounds customary for that purpose, such as, for example, compounds that form readily removable esters or carbonates. Examples include acid anhydrides of formula (R$_{10}$—CO)$_2$O and acid chlorides of formula R$_{10}$—CO—Cl, wherein R$_{10}$ is C$_1$-C$_4$alkyl or C$_1$-C$_4$alkoxy.

R$_8$ and R$_9$ are preferably each independently of the other hydrogen, C$_1$-C$_4$alkylcarbonyl or C$_1$-C$_4$alkoxycarbonyl, especially hydrogen, acetyl or ethoxycarbonyl.

The reaction of a compound of formula (9) with a compound of formula CH$_3$—CO—CH$_2$—COOR$_2$ is effected, for example, by formation of the dianion of the latter compound by means of a strong base, and reaction of the dianion with a compound of formula (9). There come into consideration as strong bases, for example, n-butyllithium, lithium diisopropylamide and sodium hydride. Sodium hydride forms only the monoanion, with the result that, when it is used, a further base, such as n-butyllithium or lithium diisopropylamide, is used for the formation of the dianion from the monoanion. The reactions as a whole can be carried out at a temperature of from −80 to 25° C. in an anhydrous, inert organic solvent, such as tetrahydrofuran, diethyl ether or 1,2-dimethoxyethane, in an inert gas atmosphere. The compound so obtained can be intercepted using a readily removable protecting group and then the double bond can be introduced under acidic or basic conditions in an inert solvent, such as tetrahydrofuran, diethyl ether, 1,2-dimethoxyethane or toluene. The protected enol can then be hydrolysed likewise under basic or acidic conditions. It is also possible to hydrolyse the intermediate dianion and eliminate the alcohol under acidic conditions.

According to a further process variant c) for the preparation of compounds of formula (2), a compound of formula

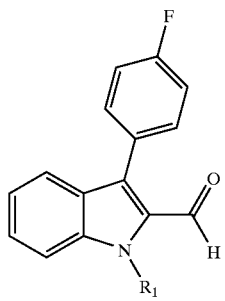

(9)

is reacted with a compound of formula

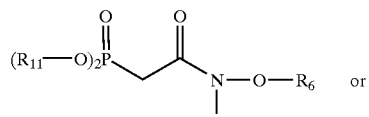

(11a)

or

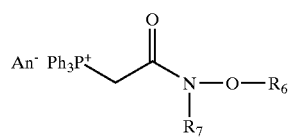

(11b)

to form a compound of formula

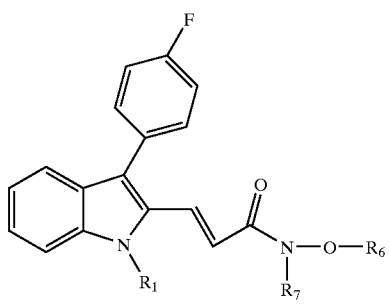

(8)

and that compound is reacted with a compound that introduces the radical of formula —CH$_2$—COOR$_2$ wherein R$_1$ and R$_2$ have the meanings and preferred meanings given hereinbefore, R$_6$ and R$_7$ are hydrogen or hydrocarbon radicals, R$_{11}$ is C$_1$-C$_4$alkyl or phenyl, especially methyl or ethyl, preferably ethyl, Ph is phenyl and An$^-$ is an anion.

R$_6$ and R$_7$ have the meanings and preferred meanings indicated hereinbefore. R$_6$ and R$_7$ are preferably C$_1$-C$_6$alkyl, especially methyl or ethyl, preferably methyl.

In the compound of formula (11b), there comes into consideration as anion especially halogen, such as bromine or preferably chlorine.

The reaction of the compound of formula (9) with a compound of formula (11a) or (11b) is generally carried out in the presence of a base, such as n-butyllithium or especially sodium hydride, in an organic solvent, such as an ether, for example diethyl ether or tetrahydrofuran, at a temperature of, for example, from −10 to 30° C. Corresponding reactions are described in J. Boutagy, Chemical Reviews, Vol. 74, No. 1, 87–99 (1974).

It is preferable in this process variant to carry out the reaction of a compound of formula (9) with a compound of formula (11a).

The reaction of the compound of formula (8) to form the compound of formula (2) can be carried out as described hereinabove.

For the preparation of compounds of formula (2), preference is given to process variants a) and b), especially process variant a).

The compounds of formula (3) may be obtained in the form of a racemate or in the form of enantiomerically pure compounds of formula (3a) in the following (R) configuration

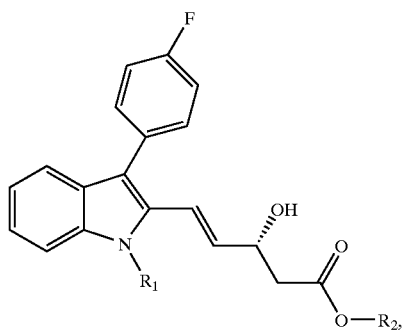
(3a)

or especially in the form of enantiomerically pure compounds of formula (3b) in the following (S) configuration

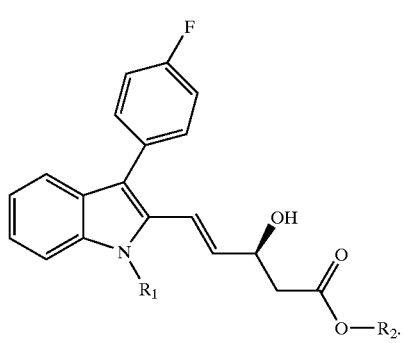
(3b)

The racemate can be resolved into the optically pure antipodes by means of known methods for the separation of enantiomers, for example by means of preparative chromatography using chiral supports (HPLC) or by esterification and crystallisation out using optically pure precipitating agents, for example D-(−) or L-(−)-mandelic acid or (+)- or (−)-10-camphor-sulfonic acid.

Enantiomerically pure or stereoisomerically pure compounds are to be understood here and hereinafter as compounds that are in at least 60%, especially 80% and, preferably, 90% pure form. Especially preferably they are in at least 95%, preferably 97.5% and, especially, 99% enantiomerically pure or stereoisomerically pure form.

The compounds of formula (1) may be obtained in the form of a mixture of stereoisomers or in pure form, especially in the following (3R,5S) configuration:

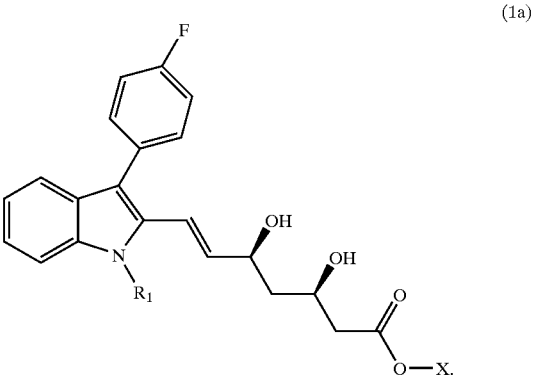
(1a)

Further stereoisomers that may be mentioned are those of the corresponding (3R,5R), (3S,5S) and (3S,5R) configurations.

Stereoisomerically pure compounds of formula (1), such as those of formula (1a), can be obtained according to procedures known for that purpose. Racemate cleavage can be carried out as indicated above under formulae (3a) and (3b).

The present invention relates also to the novel compounds of formulae (2), (3), (5) and (8), to processes for the preparation thereof, and also to the use of compounds of formula (2), (3), (5) or (8) as intermediates in the preparation of compounds of formula (1). The present invention relates also to the use of compounds of formula (5) or (8) as intermediates in the preparation of compounds of formula (2).

The preferred meanings mentioned hereinabove apply to the novel compounds of formulae (2), (3), (5) and (8).

As process for the preparation of compounds of formula (2) there comes into consideration, for example, the preparation according to process variant a), b) or c), especially according to process variant a) or b), preferably according to process variant a).

As process for the preparation of compounds of formula (3) there comes into consideration, for example, the reduction of the compound of formula (2). Preferably, the preparation of the compound of formula (2) is in that case carried out according to process variant a), b) or c), especially according to process variant a) or b), preferably according to process variant a).

As process for the preparation of compounds of formula (5) there comes into consideration, for example, the above-described halogenation, especially bromination, of the corresponding compound wherein Y is hydrogen.

As process for the preparation of compounds of formula (8) there comes into consideration especially the reaction of a compound of formula (5) with a compound that introduces the radical of formula —CH=CH—CO—N(OR$_6$)R$_7$ or the reaction of a compound of formula (9) with a compound of formula (11a) or (11b), preference being given to the first-mentioned reaction.

The following Examples illustrate the invention:

EXAMPLE 1

3-(4-Fluorophenyl)-1-isopropyl-1H-indole-2-carbaldehyde

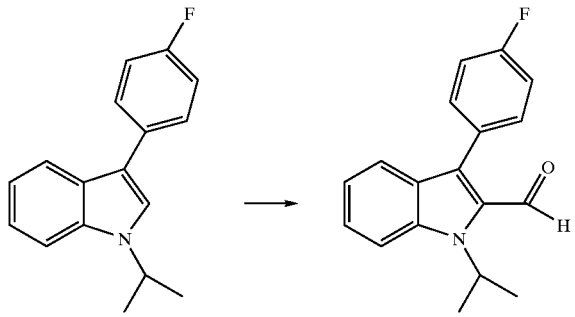

5.77 g (78.96 mmol) of DMF are weighed into a 100 ml three-necked round-bottomed flask, equipped with a magnetic stirrer, thermometer, dropping funnel, reflux condenser and nitrogen delivery line, and cooled, with stirring, to 3° C. 12.11 g (78.96 mmol) of phosphorus oxychloride are then slowly added dropwise so that the internal temperature does not exceed 10° C. The reaction mixture is then heated to 80° C. and 10 g (39.48 mmol) of 3-(4-fluorophenyl)-1-isopropyl-1H-indole, dissolved in 10 ml of DMF, are added dropwise in the course of 30 min. Stirring is subsequently carried out for 1.5 hours at that temperature. Cooling and dilution with 10 ml of DMF are then carried out. The reaction mixture is transferred into a dropping funnel and, with stirring, slowly added dropwise at 40° C. to 10 g (0.25 mol) of sodium hydroxide in 200 ml of water. The aqueous phase is extracted four times with 50 ml of toluene and the combined organic phases are washed six times with 100 ml of water. Subsequently, 10 g of silica gel are added, the mixture is stirred for 1 hour and filtration is carried out, followed by washing three times with 50 ml of toluene and concentration by evaporation. 10.17 g of a brown oil are obtained, which is dissolved in 100 ml of hexane under reflux. 10 g of silica gel are added, and filtration is carried out while hot, followed by washing three times with 50 ml of hot hexane. The filtrate is concentrated by evaporation and the residue is recrystallised from 94% ethanol. Slightly beige crystals having a melting point of from 89.5 to 91° C. are obtained.

EXAMPLE 2

5-[3-(4-Fluorophenyl)-1-isopropyl-1H-indol-2-yl]-3-methylhex-2-enoic Acid Methyl Ester

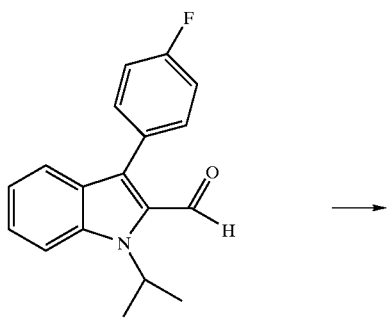

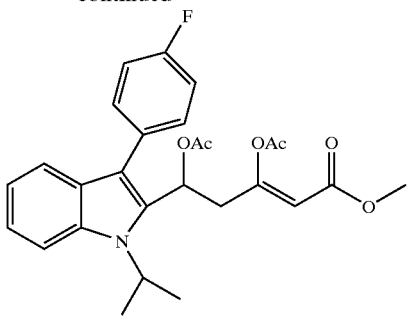

3.85 g (88.16 mmol) of sodium hydride (55%) are introduced into a thoroughly heated, 500 ml three-necked round-bottomed flask, equipped with a thermometer, dropping funnel, septum, nitrogen delivery line and magnetic stirrer, and washed twice with 25 ml of pentane. The pentane is removed using a pipette and the sodium hydride is blown dry with nitrogen. 100 ml of THF, rendered absolute using sodium, are then added, and the suspension is cooled to 5° C. by means of an ice bath with stirring. 10.24 g (88.16 mmol) of methyl acetoacetate dissolved in 50 ml of absolute THF are then slowly added dropwise so that the internal temperature does not exceed 10° C. The suspension is stirred for 30 min. while cooling with ice. 56.3 ml (90.12 mmol) of butyllithium (1.6M in hexane) are slowly added dropwise to the almost clear solution so that the internal temperature does not exceed 10° C. The clear yellow solution is stirred for 20 min. while cooling with ice. 15.0 g (53.32 mmol) of 3-(4-fluorophenyl)-1-isopropyl-1H-indole-2-carbaldehyde dissolved in 100 ml of absolute THF are added dropwise over a period of 5 min., in the course of which the internal temperature rises to 10° C. After 45 min., a thick yellow suspension has formed to which 54.4 g (533.2 mmol) of acetic anhydride are added dropwise so that the internal temperature does not exceed 10° C. The slightly turbid, yellow solution is stirred for 15 min. and then warmed to room temperature. The reaction mixture is poured into 250 ml of 1N hydrochloric acid and extracted 3 times with ethyl acetate. The combined organic phases are washed twice with 50 ml of saturated sodium chloride solution, once with 100 ml of 5% sodium hydrogen carbonate solution and three times with saturated sodium chloride solution in order to render neutral, dried over magnesium sulfate, filtered and concentrated by evaporation at 80° C. An orange oil is obtained which, according to NMR, also contains already eliminated product ((E)-5-[3-(4-fluorophenyl)-1-isopropyl-1H-indol-2-yl]-3-methylpenta-2,4-dienoic acid methyl ester).

EXAMPLE 3

(E)-5-[3-(4-Fluorophenyl)-1-isopropyl-1H-indol-2-yl]-3-methylpenta-2,4-dienoic Acid Methyl Ester

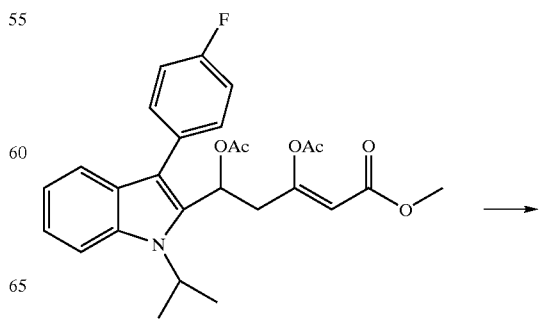

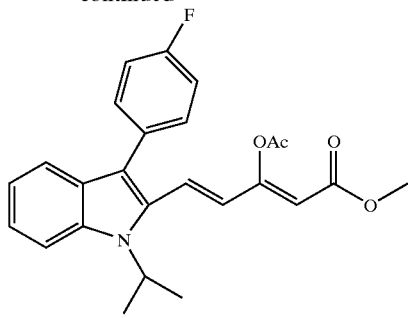

2.0 g of crude 5-[3-(4-fluorophenyl)-1-isopropyl-1H-indol-2-yl]-3-methylhex-2-enoic acid methyl ester in 50 ml of toluene are introduced into a 100 ml three-necked round-bottomed flask, equipped with a magnetic stirrer, thermometer, reflux condenser and nitrogen delivery line, 0.9 g (8.87 mmol) of triethylamine are added and the yellow solution is heated at reflux with stirring. After 2 hours, the reaction mixture is cooled, diluted with 50 ml of toluene, washed once with 100 ml of 1N hydrochloric acid and three times with 50 ml of water and concentrated by evaporation using a rotary evaporator. The crude product (orange oil) is purified by means of flash chromatography (hexane/ethyl acetate=10:1). An orange resin is obtained which, according to NMR, contains approximately 30% (E)-5-[3-(4-fluorophenyl)-1-isopropyl-1H-indol-2-yl]-3-oxopent-4-enoic acid methyl ester (mixture of keto and enol forms).

EXAMPLE 4

(E)-5-[3-(4-Fluorophenyl)-1-isopropyl-1H-indol-2-yl]-3-oxopent-4-enoic Acid Methyl Ester

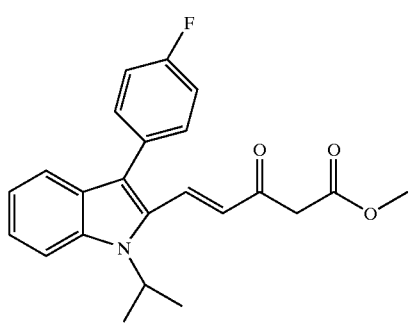

0.63 g (1.49 mmol) of (E)-5-[3-(4-fluorophenyl)-1-isopropyl-1H-indol-2-yl]-3-methylpenta-2,4-dienoic acid methyl ester in 20 ml of THF are introduced into a 50 ml round-bottomed flask equipped with a magnetic stirrer and nitrogen delivery line, 4 ml of 1N ammonium hydroxide solution are added, and the mixture is stirred for 6 hours at room temperature. The reaction mixture is poured into 200 ml of saturated sodium chloride solution and extracted twice with 100 ml of ethyl acetate, and the organic phase is washed three times with 50 ml of water, dried over magnesium sulfate, filtered and concentrated by evaporation. The crude product is purified by means of flash chromatography (hexane/ethyl acetate=9:1). An orange resin is obtained which, according to NMR, is the product in a keto-enol equilibrium of approximately 3:1.

EXAMPLE 5

(E)-5-[3-(4-Fluorophenyl)-1-isopropyl-1H-indol-2-yl]-3-oxopent-4-enoic Acid Methyl Ester

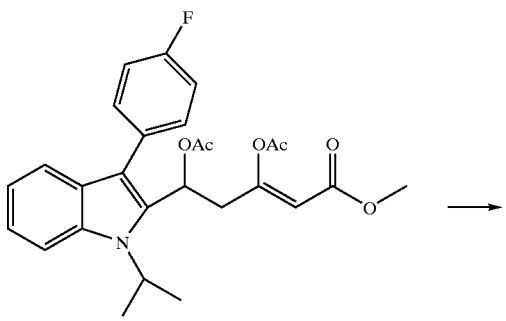

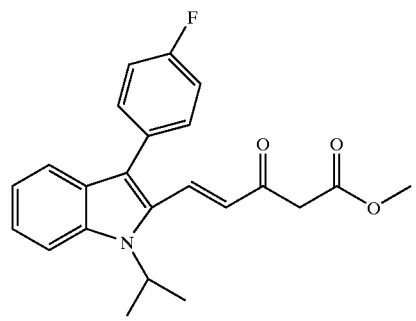

In a 2 liter round-bottomed flask equipped with a magnetic stirrer and nitrogen delivery line, 30.5 g of crude 5-[3-(4-fluorophenyl)-1-isopropyl-1H-indol-2-yl]-3-methylhex-2-enoic acid methyl ester are dissolved in 250 ml of THF, 13.49 g (133.3 mmol) of triethylamine are added and the yellow solution is heated under reflux for 2 hours. The reaction mixture is then cooled to room temperature, 53 ml (212 mmol) of 4N ammonium hydroxide solution are added and the mixture is stirred vigorously for 3 hours. The reaction mixture is then poured into 1 liter of saturated sodium chloride solution and extracted three times with 250 ml of ethyl acetate. The combined organic phases are washed once with 100 ml of 1N hydrochloric acid and three times with saturated sodium chloride solution, dried over magnesium sulfate, filtered and concentrated by evaporation. The crude product (22.78 g of an orange resin) is purified by means of flash chromatography (hexane/ethyl acetate=9:1). A resin is obtained which, according to NMR, is the product in a keto-enol equilibrium of approximately 3:1.

EXAMPLE 6

5-[3-(4-Fluorophenyl)-1-isopropyl-1H-indol-2-yl]-3,5-dihydroxypent-2-enoic Acid Methyl Ester

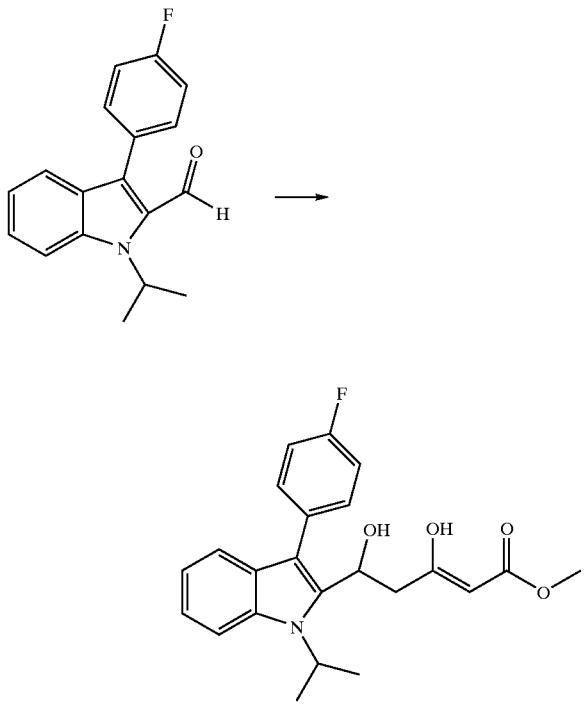

0.256 g (5.87 mmol) of sodium hydride (55%) is introduced into a thoroughly heated 100 ml three-necked round-bottomed flask, equipped with a magnetic stirrer, thermometer, dropping funnel and nitrogen delivery line, and washed twice with 5 ml of pentane. The pentane is removed using a pipette and the sodium hydride is blown dry with nitrogen. 20 ml of THF, rendered absolute using sodium, are then added, and the suspension is cooled to 3° C. by means of an ice bath with stirring. 0.68 g (5.87 mmol) of methyl acetoacetate dissolved in 5 ml of absolute THF is then slowly added dropwise so that the internal temperature does not exceed 5° C. The suspension is stirred for 15 min. while cooling with ice. 3.75 ml (6.0 mmol) of butyllithium (1.6M in hexane) are slowly added dropwise to the almost clear solution so that the internal temperature does not exceed 5° C. The clear yellow solution is stirred for 20 min. while cooling with ice. 1.0 g (3.55 mmol) of 3-(4-fluorophenyl)-1-isopropyl-1H-indole-2-carbaldehyde dissolved in 5 ml of absolute THF are added dropwise over a period of 2 min., in the course of which the internal temperature rises to 10° C. After 4 hours, the reaction mixture is poured into 100 ml of ice-water, stirred for 10 min. and extracted 3 times with 100 ml of ethyl acetate. The combined organic phases are washed twice with 100 ml of saturated sodium chloride solution in order to render neutral, dried over magnesium sulfate, filtered and concentrated by evaporation at 80° C.

An orange resin is obtained, which is in the enol form according to NMR and which is used further without being purified.

EXAMPLE 7

(E)-5-[3-(4-Fluorophenyl)-1-isopropyl-1H-indol-2-yl]-3-oxopent-4-enoic Acid Methyl Ester

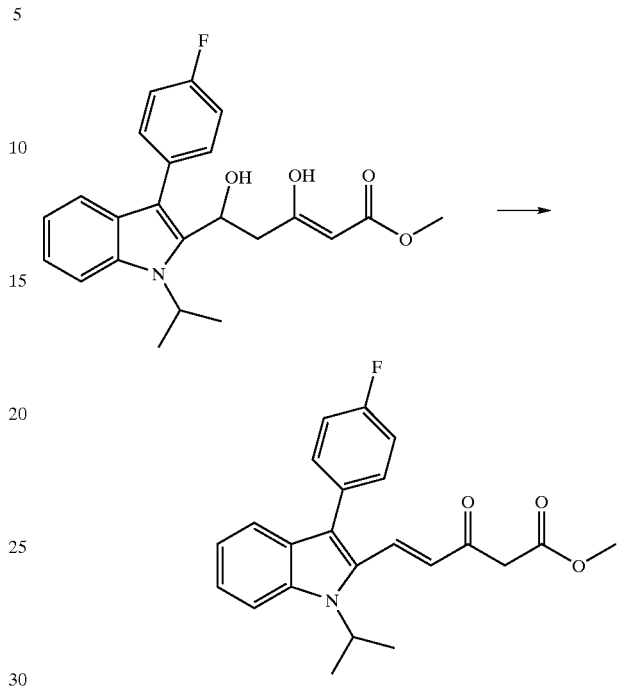

1 g of crude 5-[3-(4-fluorophenyl)-1-isopropyl-1H-indol-2-yl]-3,5-dihydroxypent-2-enoic acid methyl ester in 50 ml of toluene are introduced into a 100 ml three-necked round-bottomed flask equipped with a magnetic stirrer, thermometer, reflux condenser and nitrogen delivery line, 48 mg (0.025 mmol) of toluene-4-sulfonic acid are added and the mixture is stirred for 4 hours under reflux. The mixture is then cooled to room temperature, washed once with 25 ml of saturated sodium hydrogen carbonate solution and twice with 50 ml of saturated sodium chloride solution, dried over magnesium sulfate, filtered and concentrated by evaporation. The crude product is purified by means of flash chromatography (hexane/ethyl acetate=9:1). An orange resin is obtained which, according to NMR, is the product in a keto-enol equilibrium of approximately 3:1.

EXAMPLE 8

3,5-Bis-ethoxycarbonyloxy-5-[3-(4-fluorophenyl)-1-isopropyl-1H-indol-2-yl]-pent-2-enoic Acid Methyl Ester

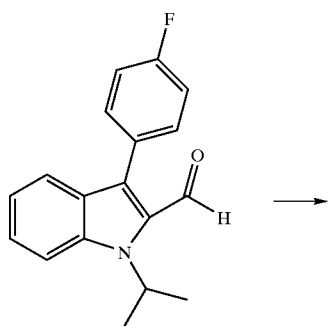

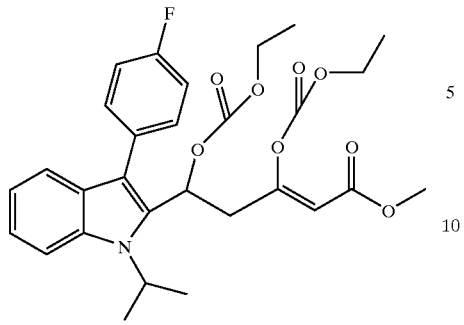

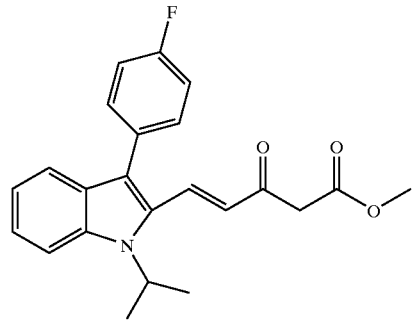

0.256 g (5.87 mmol) of sodium hydride (55%) are introduced into a thoroughly heated 100 ml three-necked round-bottomed flask, equipped with a magnetic stirrer, thermometer, dropping funnel and nitrogen delivery line, and washed twice with 5 ml of pentane. The pentane is removed using a pipette and the sodium hydride is blown dry with nitrogen. 20 ml of THF, rendered absolute using sodium, are then added, and the suspension is cooled to 3° C. by means of an ice bath with stirring. 0.68 g (5.87 mmol) of methyl acetoacetate dissolved in 5 ml of absolute THF are then slowly added dropwise so that the internal temperature does not exceed 5° C. The suspension is stirred for 15 min. while cooling with ice. 3.75 ml (6.0 mmol) of butyllithium (1.6M in hexane) are slowly added dropwise to the almost clear solution so that the internal temperature does not exceed 5° C. The clear yellow solution is stirred for 20 min. while cooling with ice. 1.0 g (3.55 mmol) of 3-(4-fluorophenyl)-1-isopropyl-1H-indole-2-carbaldehyde dissolved in 10 ml of absolute THF are added dropwise over a period of 2 min., in the course of which the internal temperature rises to 10° C. After 1.5 hours, the reaction mixture is cooled to –10° C., 5.39 g (49.7 mmol) of ethyl chloroformate are added dropwise and stirring is carried out for 30 min. at –10° C. Heating to room temperature is then carried out, 15 ml of water, 10 ml of 2N hydrochloric acid and 25 ml of acetone are added and stirring is carried out for 1 hour. The phases are separated, the aqueous phase is extracted three times with 50 ml of ethyl acetate and the combined organic phases are washed once with 50 ml of saturated sodium hydrogen carbonate solution and three times with 50 ml of saturated sodium chloride solution, dried over magnesium sulfate, filtered and concentrated by evaporation. An orange resin is obtained, which is virtually pure according to NMR and which is used further without being purified.

EXAMPLE 9

(E)-5-[3-(4-Fluorophenyl)-1-isopropyl-1H-indol-2-yl]-3-oxopent-4-enoic Acid Methyl Ester

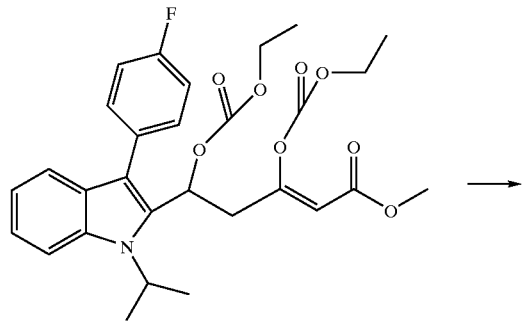

In a 100 ml three-necked, round-bottomed flask, equipped with a magnetic stirrer, thermometer, reflux condenser and nitrogen delivery line, 2.17 g of crude 3,5-bis-ethoxycarbonyloxy-5-[3-(4-fluorophenyl)-1-isopropyl-1H-indol-2-yl]-pent-2-enoic acid methyl ester are dissolved in 50 ml of DMF, 1.0 g of pyridinium p-toluenesulfonate is added and stirring is carried out for 4 hours at 80° C. The reaction mixture is then cooled, poured into 150 ml of saturated sodium chloride solution and extracted four times with 50 ml of ethyl acetate. The combined organic phases are washed six times with 50 ml of water, dried over magnesium sulfate, filtered and concentrated by evaporation. The crude product (brownish-orange resin) is purified by means of flash chromatography (hexane/ethyl acetate= 10:1). An orange resin is obtained which, according to NMR, is the product in a keto-enol equilibrium of approximately 3:1.

EXAMPLE 10

2-Bromo-3-(4-fluorophenyl)-1-isopropyl-1H-indole

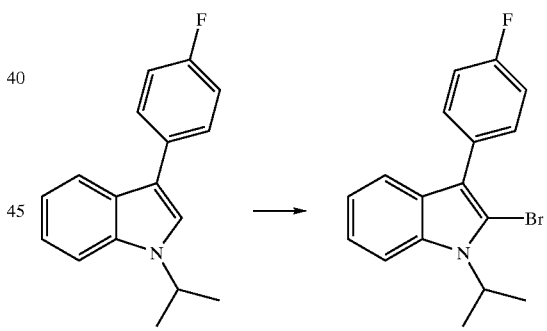

20 g (78.95 mmol) of 3-(4-fluorophenyl)-1-isopropyl-1H-indole, 200 ml of THF and 200 ml of chlorobenzene are introduced into a 1.5 liter sulfonating flask, equipped with an anchor stirrer, thermometer and nitrogen delivery line, and cooled to 3° C. with stirring. 26.58 g (78.95 mmol) of pyridinium bromide perbromide are then added and stirring is carried out for 1.25 hours at 3° C. 680 g of a 5% sodium hydrogen carbonate solution are then added dropwise in the course of 10 min. The phases are separated and the aqueous phase is extracted three times with 150 ml of chlorobenzene. The combined organic phases are washed twice with 340 ml of 5% sodium hydrogen carbonate solution and twice with 220 ml of water, dried over magnesium sulfate, filtered and concentrated by evaporation. The brown residue is dissolved in 125 ml of methylene chloride, 125 ml of 94% ethanol are added and the methylene chloride is distilled off at normal pressure. The solution is cooled slowly to room temperature and then to 3° C., and the precipitate is filtered off, washed three times with 10 ml of ice-cold 94% ethanol and dried overnight at RT/125 T. Beige crystals having a melting point of from 110 to 111.5° C. are obtained. Elemental analysis: Found 4.95% H; 61.23% C; 4.04% N; 22.9% Br; 5.67% F. Theory 4.55% H; 61.46% C; 4.22% N; 24.05% Br; 5.72% F.

EXAMPLE 11

(E)-3-[3-(4-Fluorophenyl)-1-isopropyl-1H-indol-2-yl]-N-methoxy-N-methylacrylamide

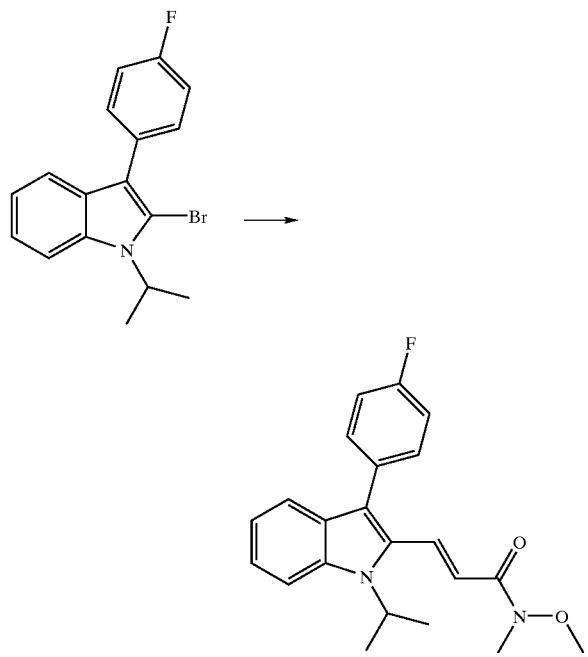

2 g (6.02 mmol) of 2-bromo-3-(4-fluorophenyl)-1-isopropyl-1H-indole and 10 ml of DMF are introduced into a 50 ml three-necked round-bottomed flask, which has been purged with nitrogen and is equipped with a magnetic stirrer, thermometer, reflux condenser, gas inlet tube and nitrogen delivery line, and degassing is carried out for 45 min. by introducing nitrogen. 24 mg (1.0 mol %) of the catalyst K4 from WO-A-99/47474 and 0.539 g (6.59 mmol) of sodium acetate are then added and degassing is carried out for a further 15 min. 1.08 g (8.43 mmol) of N-methoxy-N-methylacrylamide (prepared analogously to a procedure of S. Nahm, Tetrahedron Letters 22, 3815 (1981)) are subsequently added and the suspension is heated at reflux for 1.75 hours. A further 0.5 g (4.34 mmol) of N-methoxy-N-methylacrylamide is added and refluxing is carried out for 1.5 hours. Cooling is then carried out followed by dilution with 50 ml of water and extraction three times with 50 ml of ethyl acetate. The combined organic phases are washed three times with 50 ml of water, dried over magnesium sulfate, filtered and concentrated by evaporation. Purification by means of flash chromatography (hexane/ethyl acetate=2:1) yields a yellow solid that is pure according to NMR. Recrystallisation from 94% ethanol yields slightly yellow crystals having a melting point of from 123 to 124° C.

EXAMPLE 12

(E)-3-[3-(4-Fluorophenyl)-1-isopropyl-1H-indol-2-yl]-N-methoxy-N-methylacrylamide

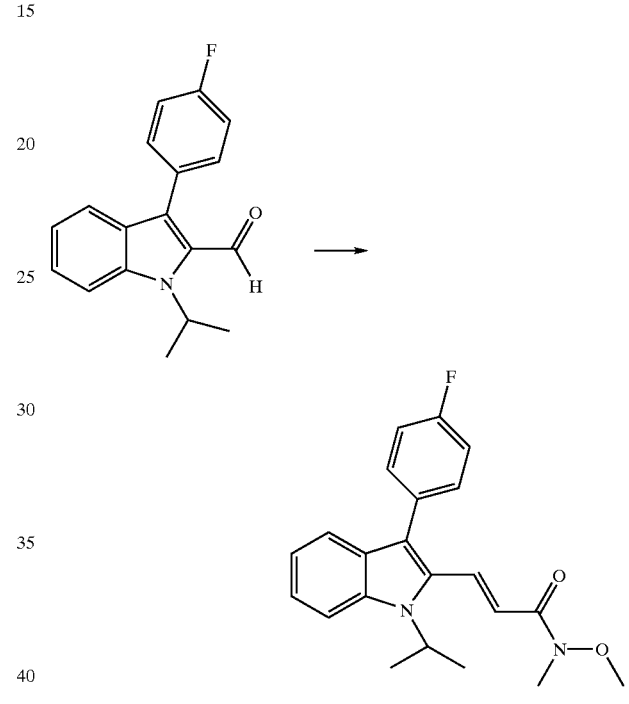

0.465 g (10.65 mmol) of sodium hydride (55%) are introduced into a 100 ml three-necked, round-bottomed flask, equipped with a magnetic stirrer, thermometer, dropping funnel and nitrogen delivery line, and washed twice with 5 ml of pentane. The pentane is removed using a pipette and the sodium hydride is blown dry with nitrogen. 10 ml of THF, rendered absolute using sodium, are added, and 1.84 g (7.46 mmol) of diethyl (N-methoxy-N-methylcarbamoyl-methyl)phosphonate dissolved in 5 ml of THF are slowly added dropwise so that the temperature does not exceed 30° C. 1 g (3.55 mmol) of 3-(4-fluorophenyl)-1-isopropyl-1H-indole-2-carbaldehyde dissolved in 10 ml of THF is then added dropwise and the clear, slightly yellow solution is stirred overnight. The reaction mixture is poured into 100 ml of water and extracted 3 times with 50 ml of ethyl acetate. The combined organic phases are washed twice with 50 ml of saturated sodium chloride solution, dried over magnesium sulfate, filtered and concentrated by evaporation. Flash chromatography (hexane/ethyl acetate=2:1) and crystallisation from 94% ethanol yields slightly yellow crystals having a melting point of from 123 to 124° C.

EXAMPLE 13

(E)-5-[3-(4-Fluorophenyl)-1-isopropyl-1H-indol-2-yl]-3-oxopent-4-enoic Acid Ethyl Ester

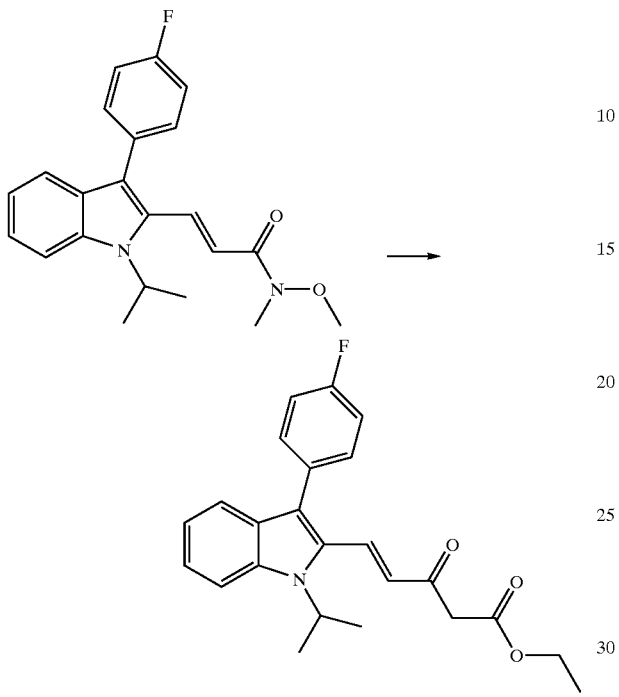

1.85 ml (12.97 mmol) of diisopropylamine, dried over KOH, in 6 ml of THF, rendered absolute using sodium, are introduced into a thoroughly heated 50 ml three-necked round-bottomed flask, equipped with a magnetic stirrer, thermometer and nitrogen delivery line, and cooled to −50° C. using an ethanol/dry-ice bath. 8.1 ml (12.97 mmol) of butyllithium (1.6M in hexane) are slowly added dropwise so that the internal temperature does not exceed −40° C. Heating to from −5 to 0° C. is carried out slowly, followed by stirring at that temperature for 30 min. Cooling to −65° C. is then carried out and 1.30 ml (12.94 mmol) of ethyl acetate are slowly added dropwise so that the internal temperature does not exceed −60° C. Stirring is subsequently carried out for 40 min. at −65° C. and then 1.20 g (3.28 mmol) of (E)-3-[3-(4-fluorophenyl)-1-isopropyl-1H-indol-2-yl]-N-methoxy-N-methylacrylamide, dissolved in 5 ml of THF, are added dropwise in the course of 25 min. and stirring is carried out for one hour at that temperature. The temperature is then increased to −5° C. in the course of 15 min. and stirring is carried out for 45 min. 8 ml of saturated ammonium chloride solution are added dropwise over a period of 3 min., in the course of which the temperature rises to 12° C. Stirring is then carried out for 15 min., 10 ml of toluene are added, the phases are separated and the aqueous phase is extracted three times with 20 ml of toluene. The combined organic phases are washed with saturated sodium chloride solution until neutral, dried over magnesium sulfate, filtered and concentrated by evaporation. Purification of the crude product by means of flash chromatography (hexane/ethyl acetate=9:1) yields a viscous orange resin which, according to NMR, is the product in a keto-enol equilibrium of approximately 3:1.

EXAMPLE 14

(E)-3-[3-(4-Fluorophenyl)-1-isopropyl-1H-indol-2-yl]-acrylic Acid

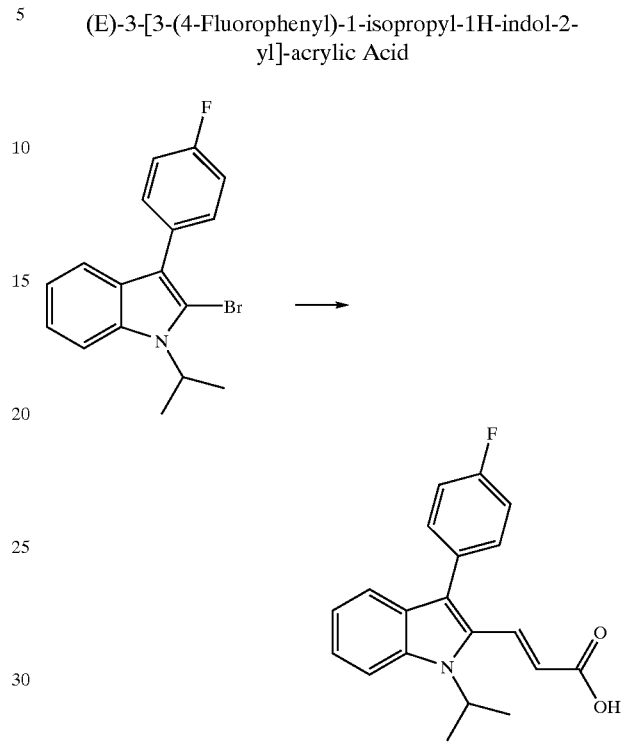

2 g (6.02 mmol) of 2-bromo-3-(4-fluorophenyl)-1-isopropyl-1H-indole, 10 ml of DMF and 0.5 ml of water are introduced into a 50 ml three-necked, round-bottomed flask, which has been purged with nitrogen and is equipped with a magnetic stirrer, thermometer, reflux condenser, gas inlet tube and nitrogen delivery line, and degassing is carried out for 30 min. by introducing nitrogen. 24 mg (1.0 mol %) of the catalyst K4 from WO-A-99/47474 and 2.15 g (6.6 mmol) of caesium carbonate are then added and degassing is carried out for a further 1 hour. 1.0 g (13.8 mmol) of acrylic acid are subsequently added and the suspension is heated at reflux for 2 hours. The DMF is then distilled off, the residue is cooled, 10 ml of 1N hydrochloric acid are added and the aqueous phase is extracted three times with 50 ml of ethyl acetate. The combined organic phases are washed three times with 30 ml of saturated sodium carbonate solution, slightly acidified again using 1N hydrochloric acid, and washed three times with 50 ml of saturated sodium chloride solution in order to render neutral. Drying over magnesium sulfate, filtration and concentration by evaporation are then carried out. The residue (1.83 g) is dissolved in THF, 5 g of silica gel are added and the solution is concentrated by evaporation using a rotary evaporator. The charged silica gel is transferred into a glass frit, and non-polar secondary products are eluted using hexane/ethyl acetate=10:1 and then the product is eluted using ethyl acetate. Concentration by evaporation yields a yellow solid which, according to NMR, is the desired product in pure form.

EXAMPLE 15

(E)-5-[3-(4-Fluorophenyl)-1-isopropyl-1H-indol-2-yl]-3-oxopent-4-enoic Acid Methyl Ester

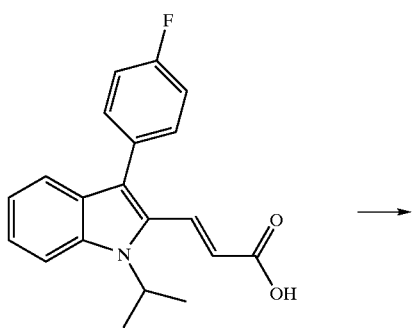

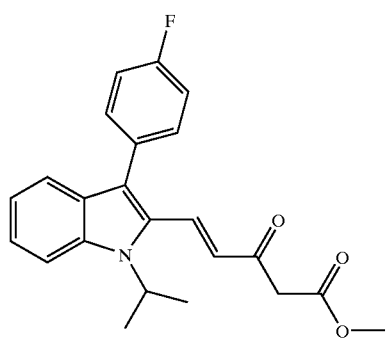

0.8 g (2.46 mmol) of (E)-3-[3-(4-fluorophenyl)-1-isopropyl-1H-indol-2-yl]-acrylic acid in 4 ml of THF are introduced into a 50 ml three-necked round-bottomed flask equipped with a magnetic stirrer, thermometer, reflux condenser and nitrogen delivery line. 0.5 g (2.96 mmol) of 1,1-carbonyldiimidazole is then added in portions in the course of 5 min. and stirring is carried out at room temperature for 1 hour. 0.24 g (2.46 mmol) of magnesium chloride and 0.39 g (2.46 mmol) of monomethyl malonate potassium salt are then added and the suspension is stirred for 24 hours at 35° C. The reaction mixture is cooled and filtered and the residue is washed twice with 25 ml of THF. The filtrate is concentrated by evaporation, taken up in 30 ml of ethyl acetate, washed with 15 ml of 1N hydrochloric acid, three times with 20 ml of saturated sodium hydrogen carbonate solution and three times with saturated sodium chloride solution, dried over magnesium sulfate, filtered and concentrated by evaporation. The residue is purified by means of flash chromatography (hexane/ethyl acetate=8:1). An orange resin is obtained which, according to NMR, is the product in a keto-enol equilibrium of approximately 3:1.

EXAMPLE 16

(E)-5-[3-(4-Fluorophenyl)-1-isopropyl-1H-indol-2-yl]-3-hydroxypent-4-enoic Acid Methyl Ester

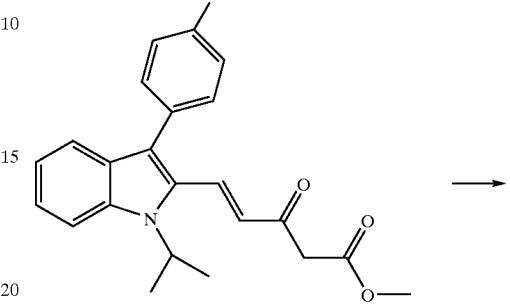

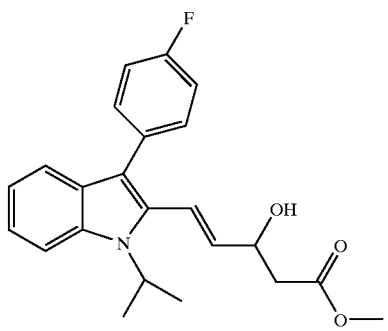

15.39 g (40.56 mmol) of (E)-5-[3-(4-fluorophenyl)-1-isopropyl-1H-indol-2-yl]-3-oxopent-4-enoic acid methyl ester in 300 ml of THF/methanol=1:1 are introduced into a 500 ml three-necked round-bottomed flask, equipped with a magnetic stirrer, thermometer and nitrogen delivery line, and cooled to −65° C. by means of an acetone/dry-ice bath. 1.84 g (48.67 mmol) of sodium borohydride are added and the solution is stirred for 1.25 hours at −65° C. The cooling means is then removed, the reaction mixture is heated to 0° C. in the course of 35 min. and is then stirred at that temperature for 35 min. The reaction mixture is poured into 24 g (0.39 mol) of acetic acid in 1.5 liters of water and extracted three times with 500 ml of ethyl acetate. The combined organic phases are washed three times with 300 ml of water, dried over magnesium sulfate, filtered and concentrated by evaporation. Purification by means of flash chromatography (hexane/ethyl acetate=3:1) yields an orange resin having an $R_f$ value of 0.23 (hexane/ethyl acetate=3:1). According to NMR the product is in pure form.

The enantiomers can be resolved by means of HPLC on a Chiracel AD column using n-hexane/ethanol=99:1 at a flow rate of 1 ml/min., the retention times being 25.29 and 28.02 min.

EXAMPLE 17

(E)-7-[3-(4-Fluorophenyl)-1-isopropyl-1H-indol-2-yl]-5-hydroxy-3-oxohept-6-enoic Acid Tert-Butyl Ester

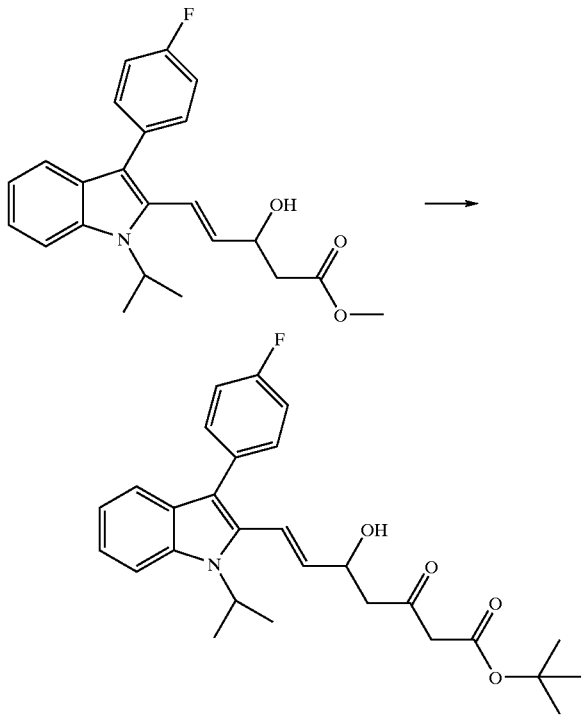

11.41 g (112.72 mmol) of diisopropylamine (dried over KOH) are weighed into a thoroughly heated 500 ml three-necked round-bottomed flask, equipped with a magnetic stirrer, thermometer, dropping funnel, nitrogen delivery line and ethanol/dry-ice bath, and 50 ml of THF (dried over sodium) are added. Under a nitrogen atmosphere, cooling to −50° C. is carried out and in the course of 30 min. 70.45 ml (112.72 mmol) of butyllithium (1.6M in hexane) is so added dropwise that the temperature remains between −55° C. and −45° C. The reaction mixture is then heated in the course of 15 min. to −5° C. and is maintained at that temperature for 30 min. It is then cooled to −65° C., 13.09 g (112.72 mmol) of tert-butyl acetate are added dropwise in the course of 30 min. and stirring is carried out at that temperature for 40 min. 10.78 g (28.18 mmol) of (E)-5-[3-(4-fluorophenyl)-1-isopropyl-1H-indol-2-yl]-3-hydroxypent-4-enoic acid methyl ester in 50 ml of THF (dried over sodium) are added dropwise in the course of 30 min. Stirring is then carried out for 1 hour at −60° C., followed by heating in the course of 45 min. to −5° C. and leaving at that temperature for 30 min. Hydrolysis with 65 ml of saturated ammonium chloride solution is carried out in the course of 3 min. and stirring is carried out for 10 min. The phases are separated and the aqueous phase is extracted twice with 250 ml of ethyl acetate. The combined organic phases are washed with 10 ml portions of 1N HCl until the pH is acidic, and then with saturated sodium chloride solution until neutral, dried over magnesium sulfate, filtered and concentrated by evaporation. An orange product is obtained which, according to NMR, still contains tert-butyl acetate.

The enantiomers can be resolved by means of HPLC on a Chiracel OD column using n-hexane/ethanol=98:2 at a flow rate of 1 ml/min., the retention times being 21.68 and 28.02 min.

EXAMPLE 18

Erythro-(+/−)-(E)-7-[3-(4-Fluorophenyl)-1-isopropyl-1H-indol-2-yl]-3,5-dihydroxyhept-6-enoic Acid Tert-Butyl Ester

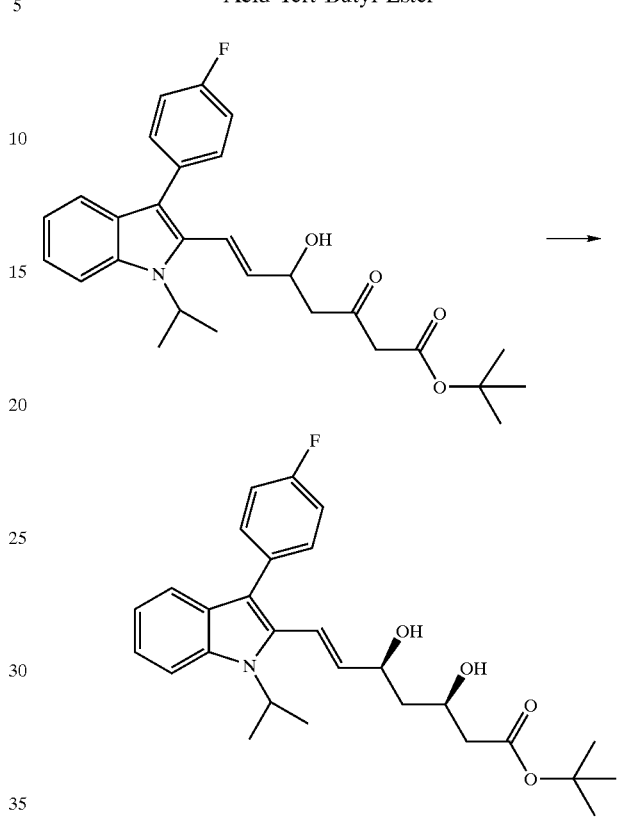

100 ml of THF (dried over sodium) are introduced into a thoroughly heated 500 ml three-necked, round-bottomed flask, equipped with a magnetic stirrer, thermometer, dropping funnel, nitrogen delivery line and acetone/dry-ice bath, and cooled under a nitrogen atmosphere and with stirring to −78° C. 2.05 g (54.12 mmol) of sodium borohydride are added and stirring is carried out for 5 min. 40.59 ml (40.59 mmol) of diethyl methoxyborane (1M in THF) are added dropwise in the course of 15 min. and stirring is carried out for 15 min. 14.97 g of crude (E)-7-[3-(4-fluorophenyl)-1-isopropyl-1H-indol-2-yl]-5-hydroxy-3-oxohept-6-enoic acid tert-butyl ester dissolved in 35 ml of THF (dried over sodium) and 45 ml of methanol (dried over 4 Å molecular sieve) are then added dropwise in the course of 1 hour so that the temperature does not exceed −75° C. The reaction mixture is poured, with stirring, into a mixture of 125 ml of saturated sodium hydrogen carbonate solution and 125 ml of ethyl acetate. 150 ml of water are added to the mixture in order to dissolve precipitated salts, the phases are separated and the aqueous phase is extracted twice with 250 ml of ethyl acetate. The combined organic phases are washed four times with 50 ml of saturated sodium chloride solution, dried over magnesium sulfate, filtered and concentrated by evaporation. A yellow resin is obtained, which is dissolved in 170 ml of ethyl acetate, and 18.29 g of 30% hydrogen peroxide solution are added in the course of 20 minutes, the temperature being maintained at 20° C. by means of a water bath. Stirring is then carried out for 18 hours at room temperature, 130 ml of saturated sodium chloride solution are added, the phases are separated and the organic phase is washed with 130 ml of a 10% sodium hydrogen sulfite solution so that afterwards a peroxide test with potassium iodide/starch paper is negative. Washing twice with 50 ml of saturated sodium chloride solution is then carried out, followed by drying over magnesium sulfate, filtration and concentration by evaporation. After column chromatography (hexane/ethyl acetate=3:2), the desired product is obtained, the syn/anti ratio according to $^{13}$C-NMR being>70:1 (see K. M. Chen, Tetrahedron Letters 28, 155 (1987)).

The enantiomers can be resolved by means of HPLC on a Chiracel OD column using n-hexane/ethanol=93:7 at a flow rate of 1 ml/min., the retention times being 6.93 and 8.89 min.

EXAMPLE 19

Sodium Erythro-(+/−)-(E)-7-[3-(4-fluorophenyl)-1-isopropyl-1H-indol-2-yl]-3,5-dihydroxyhept-6-enoate

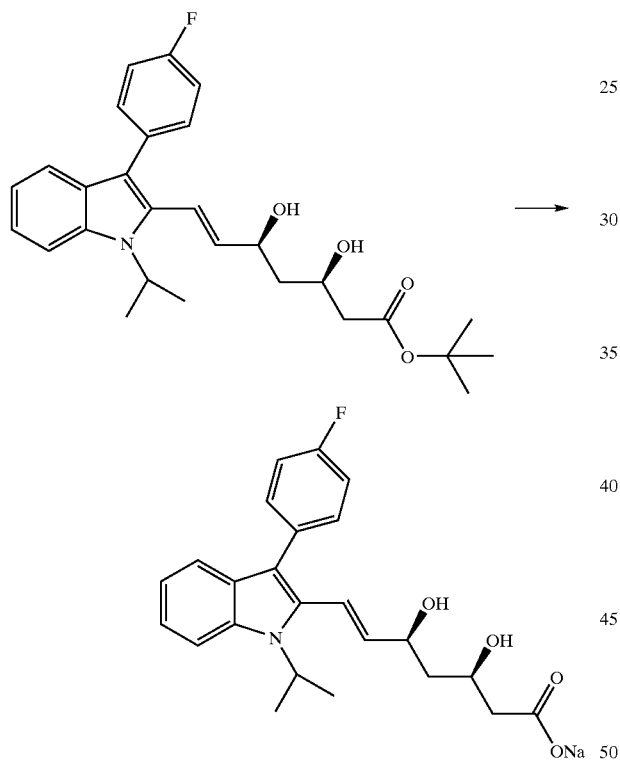

0.49 g (1.05 mmol) of erythro-(+/−)-(E)-7-[3-(4-fluorophenyl)-1-isopropyl-1H-indol-2-yl]-3,5-dihydroxyhept-6-enoic acid tert-butyl ester in 5 ml of ethanol puriss, are introduced into a 10 ml three-necked, round-bottomed flask, equipped with a magnetic stirrer, thermometer, septum, injector and nitrogen delivery line, 1.00 ml (1.00 mmol) of 1N sodium hydroxide solution is added dropwise and stirring is carried out for 2.5 hours at room temperature. The clear solution is filtered and diluted with 6 ml of water and extracted twice with 7 ml of tert-butyl methyl ether. Approximately 2 ml of water are distilled off and the remaining solution is lyophilised, yielding a slightly beige powder of which the NMR corresponds to that of the commercial product.

What is claimed is:

1. A process for the preparation of a compound of formula

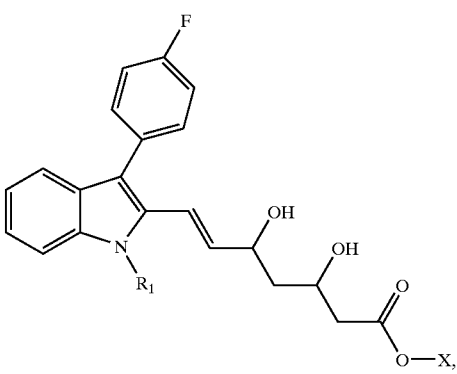

(1)

wherein $R_1$ is $C_1$–$C_6$alkyl and

X is hydrogen, a hydrocarbon radical or a cation, wherein a compound of formula

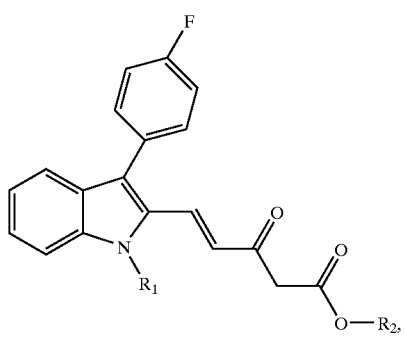

(2)

wherein $R_1$ is as defined above and $R_2$ is hydrogen or a hydrocarbon radical, is reduced, the resulting compound of formula

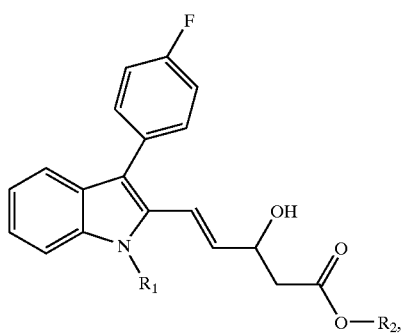

(3)

wherein $R_1$ and $R_2$ are as defined above, is reacted with a compound that introduces the radical at formula —CH$_2$COOR$_3$ wherein $R_3$ has the meanings given above for $R_2$, and the resulting compound of formula (4)

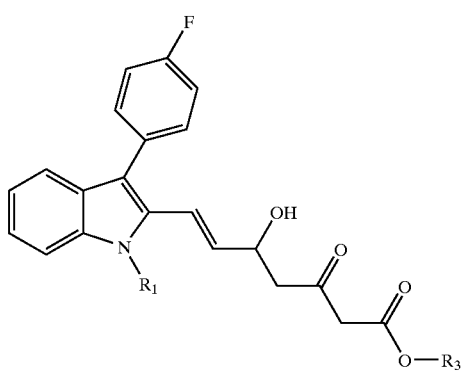

is reduced and optionally hydrolysed.

2. A process according to claim 1, wherein the compound of formula (2) is obtained by reacting a compound of formula (5)

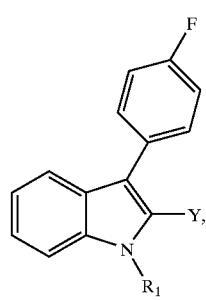

wherein $R_1$ is as defined in claim 1 and
Y is bromine, chlorine, iodine, —$OSO_2CF_3$ or —COCl, especially bromine,
with a compound that introduces the radical of formula —CH=CH—Z, wherein
Z is the radical —$COOR_4$, —$COR_5$ or —CN,
$R_4$ is hydrogen or a hydrocarbon radical and
$R_5$ is a hydrocarbon radical or unsubstituted or substituted amino,
and reacting the resulting compound of formula (6)

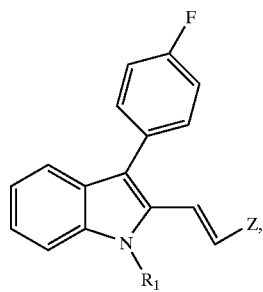

optionally after conversion of the compound of formula (6) wherein Z is the radical —$COOR_4$ into the corresponding acid chloride or into the free acid,
with a compound that introduces the radical of formula —$CH_2$—$COOR_2$ wherein
$R_2$ is as defined in claim 1.

3. A process according to claim 1, wherein the compound of formula (2) is obtained by reacting a compound of formula (9)

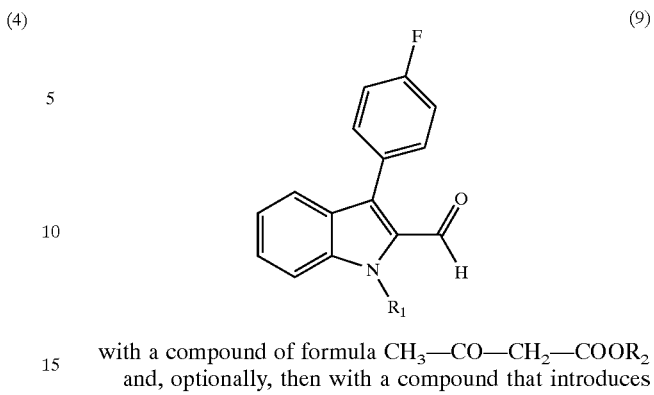

with a compound of formula $CH_3$—CO—$CH_2$—$COOR_2$ and, optionally, then with a compound that introduces a protecting group, to form a compound of formula (10)

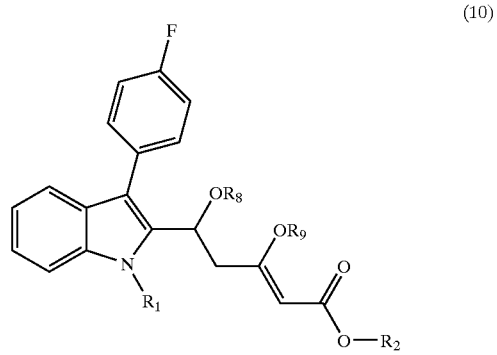

wherein $R_1$ and $R_2$ are as defined in claim 1, and
$R_8$ and $R_9$ are hydrogen or a protecting group,
introducing a double bond under acidic or basic conditions, and removing any protecting group that may be present.

4. A process according to claim 1, wherein the compound of formula (2) is obtained by reacting a compound of formula (9)

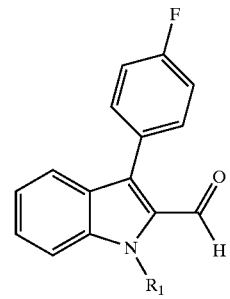

with a compound of formula (11a)

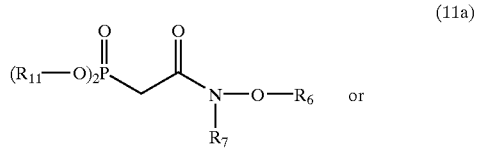   or (11b)

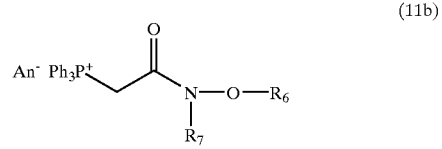

to form a compound of formula

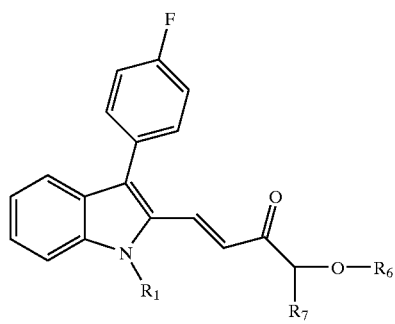

(8)

and reacting that compound with a compound that introduces the radical of formula —CH$_2$—COOR$_2$
wherein R$_1$ and R$_2$ are us defined in claim 1,
R$_6$ and R$_7$ are hydrogen or hydrocarbon radicals,
R$_{11}$ is C$_1$–C$_4$alkyl or phenyl,
Ph is phenyl and An$^-$ is an anion.

5. A process according to claim 1, wherein there is used as compound of formula (3) a compound of formula

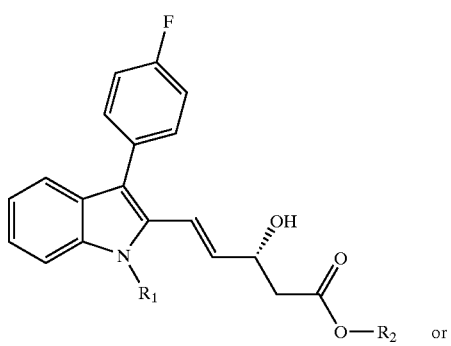

(3a)

or

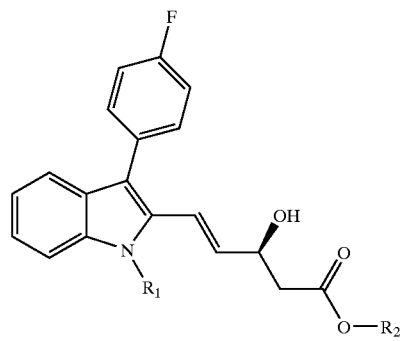

(3b)

wherein R$_1$ and R$_2$ are as defined in claim 1.

6. A process according to claim 1, wherein the compound of formula (4) is hydrolysed.

7. A process according to claim 1, wherein
R$_1$ is isopropyl.

8. A process according claim 4, wherein
R$_2$, R$_3$, R$_4$, R$_6$ and R$_7$ are C$_1$–C$_6$alkyl.

9. A process according to claim 2, wherein
R$_5$ is C$_1$–C$_6$alkyl or a radical of formula —N(OR$_6$)R$_7$ in which R$_6$ and R$_7$ are C$_1$–C$_6$alkyl.

10. A process according to claim 3, wherein
R$_8$ and R$_9$ are each independently of the other hydrogen, C$_1$–C$_4$alkylcarbonyl or C$_1$–C$_4$alkoxycarbonyl.

11. A process according to claim 2, wherein
Y is bromine.

12. A process according to claim 1, wherein
X is a sodium cation.

* * * * *

UNITED STATES PATENT AND TRADEMARK OFFICE
CERTIFICATE OF CORRECTION

PATENT NO. : 6,743,926 B2
DATED : June 1, 2004
INVENTOR(S) : Annemarie Wolleb et al.

It is certified that error appears in the above-identified patent and that said Letters Patent is hereby corrected as shown below:

<u>Title page,</u>
Please Insert Item:

-- [30]      Foreign Application Priority Data

26 May 2000       [EPO]       00810460 --.

Signed and Sealed this

Twenty-third Day of November, 2004

JON W. DUDAS
*Director of the United States Patent and Trademark Office*